United States Patent [19]

Reichert et al.

[11] 4,206,014

[45] Jun. 3, 1980

[54] PROCESS FOR REMOVING DETERGENTS FROM VIRUS-ANTIGEN SUSPENSIONS

[75] Inventors: Edgar Reichert; Mirko Majer, both of Marburg an der Lahn, Fed. Rep. of Germany

[73] Assignee: Behringwerke Aktiengesellschaft, Marburg an der Lahn, Fed. Rep. of Germany

[21] Appl. No.: 958,512

[22] Filed: Nov. 7, 1978

[30] Foreign Application Priority Data

Nov. 9, 1977 [DE] Fed. Rep. of Germany ....... 2750045

[51] Int. Cl.² .................... A61K 39/12; A61K 39/18; A61K 39/28
[52] U.S. Cl. .......................................... 424/89; 435/7; 260/112 R
[58] Field of Search .................... 424/88–92; 195/1.4–1.5

[56] References Cited

U.S. PATENT DOCUMENTS

| | | | |
|---|---|---|---|
| 3,415,804 | 12/1968 | Polson | 424/88 X |
| 3,790,552 | 2/1974 | Johnson et al. | 424/89 X |
| 3,951,937 | 4/1976 | Vnek et al. | 424/89 X |
| 3,962,421 | 6/1976 | Neurath | 424/89 |
| 3,989,818 | 11/1976 | Polson | 424/89 |
| 4,029,763 | 6/1977 | Kilbourne | 424/89 |
| 4,064,232 | 12/1977 | Bachmayer et al. | 424/89 |
| 4,102,996 | 7/1978 | McAlger et al. | 424/89 |
| 4,113,712 | 9/1978 | Funakoshi | 424/89 X |
| 4,118,478 | 10/1978 | Prince et al. | 424/89 |
| 4,118,479 | 10/1978 | Prince et al. | 424/89 |

*Primary Examiner*—Shep K. Rose
*Attorney, Agent, or Firm*—Curtis, Morris & Safford

[57] ABSTRACT

A method for isolating a detergent-free virus-antigen from a suspension of said virus-antigen containing detergent, which method comprises precipitating said virus-antigen by adding a polyethylene glycol to said suspension and then isolating the detergent-free virus-antigen precipitate by sedimentation, said detergent remaining in said suspension.

8 Claims, No Drawings

PROCESS FOR REMOVING DETERGENTS FROM VIRUS-ANTIGEN SUSPENSIONS

This invention relates to a process for removing detergents from virus-antigen suspensions containing detergents.

The influenza virus has a spherical shape and its surface is covered with stinger-like extensions, the so-called spikes, imparting to the virus the appearance of a hedgehog. The virus has two types of spikes, namely the hemagglutinin and the neuraminidase types.

Both types of spikes are glycoproteins which are responsible for the immunizing properties of an influenza vaccine. All other virus proteins are without any importance to immunization, on the contrary, by increasing the protein content they may even have a detrimental effect on the compatibility of the vaccine. It is, therefore, desirable to have an influenza vaccine which contains exclusively the two surface antigens. These surface antigens can be split selectively from the virus by various surface-active substances, so called detergents, without the remaining body of the virus being destroyed. The undamaged virus bodies can be separated by ultracentrifugation from the spikes remaining in the supernatant. A detergent which is especially suitable for the selective isolation of spikes is Triton$^{(R)}$ N-101 (nonylphenoxypolyethoxyethanol).

The suspension of spikes freed from the virus bodies by a treatment with Triton N-101 contains, of course, the Triton N-101. When the spikes, obtained in this manner, are to be used for the manufacture of a vaccine, it is necessary, for reasons of compatibility and stability, to remove the Triton N-101.

Processes have been proposed to remove the detergent Triton N-101 from split virus suspension, but these processes are rather complicated, involve great losses or are unsatisfactory. For example, a separation of phases, after reaching the turbidity point, by increasing the salt concentration has been proposed. Since the separation is not complete, a further step has to be added, for example adsorption on aluminum hydroxide, which, when carried out alone, is only effective if the Triton N-101 is contained in the mixture in a very low concentration. After adsorption on aluminum hydroxide, it is not possible to elute the antigens therefrom without important losses. A precipitation with alcohols has also been described. But in this process the danger exists that the antigens are denatured. Ultrafiltration has been proposed as well. The latter method is, however, only successful with concentrations of the detergent below the critical micelle concentration of about 0.01. Otherwise, the concentration has to be reduced, for example by dilution, so that ultrafiltration becomes lengthy and the losses are high. The removal of Triton N-101 by adsorption on Bio Beads SM2 (Bio Rad Laboratories, USA), a neutral, porous styrene-divinyl copolymer in the form of beads, is expensive. The preparation of the Bio Beads for the adsorption is complicated and it is not possible to remove in this manner Triton N-101 which is not in micelle form. Hence, with Bio Beads the Triton content can only be reduced to a concentration of about 0.01%, which is not sufficient.

The present invention provides a process for removing detergents from virus-antigen suspensions containing detergents, which comprises precipitating the virus-antigens in the detergent-containing virus-antigen suspension by the addition of polyethylene glycol, isolating the virus-antigen precipitate free from detergent by sedimentation and optionally taking up the precipitate in a liquid medium.

For precipitation, 6 to 18% and preferably 12% of polyethylene glycol are added to the suspension, the polyethylene glycol having a molecular weight above 1,000, preferably 6,000.

The process according to the invention can be used for all antigen suspensions of viruses capable of being split with Triton N-101, such as influenza viruses, parainfluenza viruses and rhabdo-viruses, for example the rabies virus. As detergent nonylphenoxypolyethoxyethanol, mostly named Triton$^{(R)}$N-101 in the literature, proved to be especially suitable. Triton is the name for a line of non-ionic, surface-active substances comprising an X and an N series. The compounds of the N-series including Triton N-101 are obtained by reaction of nonyl phenol with ethylene oxide. Triton N-101 is a nonylphenoxypolyethoxyethanol in which the syllable "poly" denotes 9 to 10 ethoxy groups. The process of the invention is also suitable for virus-antigen suspensions containing other detergents, for example Arkopal$^{(R)}$ N 110 (HOECHST AG), a non-ionic detergent, Hoe S 2407 (HOECHST AG), an anionic detergent, Genamin$^{(R)}$ 0-080 (HOECHST AG), a cationic detergent and Hoe S 1982 (HOECHST AG), an amphoteric detergent.

As a liquid medium in the sense of the invention, water and aqueous buffer solutions having a pH at which the respective antigen is the most stable can be used. The most favorable pH value for the re-suspension of influenza surface antigen is, for example, at about 7. The buffer solutions can also contain neutral salts, for example phosphate-buffered sodium chloride solution.

In the case of influenza viruses which have been split with approximately 1% of Triton N-101, it proved advantageous first to separate by centrifugation the surface antigens split from the ineffective residual virus body. The detergent remains in the supernatant suspension together with the surface antigens. Polyethylene glycol having a molecular weight above 1,000, preferably of 6,000, is then added to the suspension obtained. A practically complete precipitation (100%) is obtained with the addition of 12% of polyethylene glycol. The precipitated antigens are isolated by centrifugation and the detergent-containing supernatant is rejected. After the precipitation, Triton N-101 can no longer be detected in the precipitate.

If desired, the precipitation of virus antigens can be repeated in the same centrifuge glass by dissolving the sediment in a buffer solution and precipitating again with polyethylene glycol.

Alternatively, the sediment can be washed out with a buffer solution containing at least 1% of polyethylene glycol. When the sediment is dissolved in a buffer solution, the solution obtained is free from deterent. If desired, residues of polyethylene glycol can be removed in known manner by ultrafiltration through diaphragms of suitable pore width.

Triton N-101 can be detected by the method described by Gareval for Triton X-100 which is based on the formation of a blue precipitate due to the reaction of the polyethylene oxide groups of the Triton with cobalt cyanate. The blue color of the precipitate is washed out with ehtylene dichloride and evaluated by photometry.

The virus-antigens freed from detergents according to the invention can be processed into vaccines in known manner.

The following examples illustrate the invention.

EXAMPLE 1

Influenza virus A Victoria was propagated in known manner for 2 days at 35° C. in embryonated hens' eggs. The virus-containing allantoic fluids were harvested and mixed. The virus was purified in an Electronucleionics Ultracentrifuge, model K2, and concentrated.

10 ml=1% of Triton N-101 was added to one liter of the virus concentrate. After the concentrate had stood for 3 hours at 40° C., the virus bodies freed from spikes were allowed to deposit as sediment for 1 hour at 53,700 g and the sediment was rejected. 120 g=12% of polyethylene glycol having a molecular weight of 6,000 were then added to the supernatant and, after a time of incubation of 18 hours at 4° C., the precipitated spikes were allowed to deposit as sediment for 30 minutes at 10,000 revolutions per minute. The sediment was taken up in phosphate-buffered sodium chloride solution. It contained both types of spikes of the virus, i.e. the neuraminidase and the hemagglutinin. Triton could no longer be detected in the suspension. As a test, the method of Gareval was used, according to which the limit of detection is 0.005% of Triton N-101. On the other hand, the Triton N-101 used could be found quantitatively in the supernatant after the precipitation with polyethylene glycol.

The hemagglutinin was identified by the Radial-Diffusion Test according to Schild against anti-hemagglutinin serum. Three bands were found by polyacrylamide gel electrophoresis, which bands can be atttributed to the two types of hemagglutinin and the neuraminidase and are typical of the examined glycoproteins.

The isolated virus antigen was administered subcutaneously in an amount of 1 ml, undiluted and in the dilutions $10^{-1}$ and $10^{-2}$, to two rabbits each. After three weeks, the hemagglutinin inhibition antibody titers of the rabbit sera were measured. They were found to be 128, 64 and 16, which means that even in the high dilution an antigen-antibody reaction had taken place.

EXAMPLE 2

Influenza virus B Hongkong was treated with polyethylene glycol 6,000 in the manner described in Example 1. With this virus, too, no Triton N-101 could be detected in the sediment.

EXAMPLE 3

Sendai virus strain 52 was treated with polyethylene glycol 6,000 in the manner described in Example 1. With this virus, too, no Triton N-101 could be detected in the sediment after the treatment.

EXAMPLE 4

Rabies virus of the strain Pitman-Moore, propagated in human diploid cells strain WI-38 were treated in the manner described in Example 1 with Triton N-101 and subsequently with polyethylene glycol. In the antigen suspension obtained, no Triton could be detected. The surface antigen could be detected as a typical band in electrophoresis.

EXAMPLE 5

Influenza virus A Victoria was split overnight with 2% of Triton. Under these conditions the spikes were removed from the virus bodies and simultaneously the virus bodies were split. By working up the Triton-containing suspension of all virus-antigens in the manner described in Example 1, a sediment was obtained which contained all virus-antigens but was free from Triton.

EXAMPLE 6

1 liter of a virus concentrate of influenza virus A Victoria, obtained as described in Example 1, was treated with 10 g of Arkopal N 110. After precipitation by means of 12% of polyethylene glycol, Arkopal N 110 could no longer be detected in the antigen suspension.

EXAMPLE 7

Analogous experiments were carried out with the detergents Hoe S 2407, Genamin 0-080 and Hoe S 1982. In all experiments no detergent could be detected after the polyethylene glycol precipitation.

EXAMPLE 8

In the manner described in Example 1, spikes of influenza virus A Victoria were precipitated with
polyethylene glycol 1,550
polyethylene glycol 4,000
polyethylene glycol 20,000 and
polyethylene glycol 40,000.

In all experiments the sediment contained the virus-antigens free from detergent.

EXAMPLE 9

In the manner described in Example 4, the antigens of the rabies virus strain Pitman-Moore, obtained by means of Triton N-101, were precipitated with
polyethylene glycol 1,500
polyethylene glycol 4,000
polyethylene glycol 20,000 and
polyethylene glycol 40,000.

In all experiments the sediment contained the virus antigens free from detergent.

What is claimed is:

1. A method for isolating a detergent-free virus-antigen of an influenza virus, of a para-influenza virus, or of a rhabdo virus, from a suspension of said virus-antigen containing detergent, which method comprises precipitating said virus-antigen by adding 6 to 18 percent of polyethylene glycol having a molecular weight between 1000 and 40000 to said suspension and then isolating the detergent-free virus-antigen precipitate by sedimentation, said detergent remaining in said suspension.

2. The method of claim 1 wherein said virus is an influenza virus.

3. The method of claim 1 wherein said detergent is nonylphenoxypolyethoxyethanol.

4. A method for isolating a virus-antigen of an influenza virus from a suspension of said virus-antigen containing nonylphenoxypolyethoxyethanol as a detergent, which method comprises precipitating said virus-antigen by adding 6 to 18 percent of polyethylene glycol having a molecular weight of about 6000 to said suspension and then isolating the detergent-free virus-antigen precipitate by sedimentation, said detergent remaining in said suspension.

5. The method of claim 1 wherein the virus-antigen precipitate is taken up in a liquid medium.

6. The method of claim 5 wherein water or an aqueous buffer solution is used as the liquid medium.

7. The method of claim 1 wherein the virus-antigens are precipitated by the addition of 12% of polyethylene glycol.

8. The method of claim 1 wherein the polyethylene glycol has a molecular weight of 6,000.

* * * * *